United States Patent [19]
Pilleux et al.

[11] Patent Number: 5,346,693
[45] Date of Patent: Sep. 13, 1994

[54] DEPIGMENTING COSMETIC OR DERMATOLOGICAL COMPOSITION CONTAINING ARBUTOSIDE DERIVATIVES

[75] Inventors: Eric Pilleux, Paris; Ming Li, Gif-sur-Yvette; Jean-Pierre Cosson, Nouméa; Daniel Guénard, Montrouge; Thierry Sevenet; Pierre Potier, both of Paris, all of France

[73] Assignee: L'Oreal, Paris, France

[21] Appl. No.: 913,955

[22] Filed: Jul. 17, 1992

[30] Foreign Application Priority Data

Jul. 19, 1991 [FR] France ................. 91 09188

[51] Int. Cl.$^5$ ................................. A61K 7/135
[52] U.S. Cl. ...................... 424/62; 424/401; 424/450; 514/844; 514/938
[58] Field of Search ............ 424/62, 401, 450; 514/844, 938

[56] References Cited

U.S. PATENT DOCUMENTS 4,503,041  3/1985  Kashiwayama .............. 424/115
4,764,505  8/1988  Fujinuma et al. ............. 514/35

FOREIGN PATENT DOCUMENTS 62-215512  9/1987  Japan.
63-008314  1/1988  Japan.

OTHER PUBLICATIONS

CA 98(3): 14304n (1983).
CA 112(1): 4518d (1990).
CA 87(7): 49555v (1977).
CA 112(7): 52183n (1990).
CA 99(19): 155113g (1983).
M. Varma et al., "The Synthesis of 2- and 6-0-p-Coumaroyl and 6-0-p-Hydroxybenzoyl Arbutin Derivatives", *Monatshefte fur Chemie* 111, 469–473 (1980).
T. Iwagawa et al., "Phenolic Constituents of Viburnum Carlesii", *Rep. Fac. Sci. Kagoshima University* (Math., Phys. & Chem.), No. 21, pp. 89–95, 1988.
Haslam et al., "Phenolic Constituents of Vaccinium Vitis idaea L.", *J. Chem. Soc.*, Suppl. I, 1964, pp. 5649–5654.
Manju et al., "New Arbutin Derivatives from Leaves of Grevillea Robusta and Hakea Saligna", *Phytochemistry*, vol. 16, 1977, pp. 793–794.
Machida et al., "Phenolic Glycosides from Viburnum Dilatatum", *Phytochemistry*, vol. 30, No. 6, 1991, pp. 2013–2014.

*Primary Examiner*—Thurman K. Page
*Assistant Examiner*—Jyothsna Venkat
*Attorney, Agent, or Firm*—Oliff & Berridge

[57] ABSTRACT

A cosmetic or dermatological composition contains as an active ingredient at least one arbutoside derivative with the following general formula:

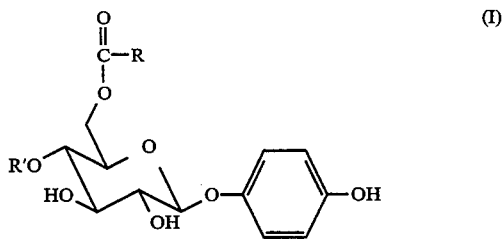

wherein:
R represents an unsaturated aliphatic or aromatic hydroxylated residue having 4 to 16 carbon atoms, and R' represents a hydrogen atom or the

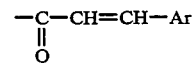

radical.

Ar represents a phenyl radical that may be substituted by one or more hydroxyl groups. Applications of the composition include the bleaching of skin and the treatment of pigmented spots.

10 Claims, No Drawings

DEPIGMENTING COSMETIC OR DERMATOLOGICAL COMPOSITION CONTAINING ARBUTOSIDE DERIVATIVES

The present invention relates to a cosmetic or dermatological composition with a depigmenting action containing, as an active ingredient, at least one derivative of arbutoside or arbutin. The composition according to the invention is intended in particular to bleach the skin or to treat pigmented spots.

BACKGROUND OF THE INVENTION

The mechanism by which skin pigmentation is formed, namely by which melanins are formed, is particularly complex and schematically involves the following main steps:

with the enzyme involved in this series of reactions being essentially tyrosinase.

The substances in widest use at the present time as depigmentors are in particular hydroquinone and its derivatives, particularly its ethers such as hydroquinone monomethylether.

These compounds, while they are definitely effective, are unfortunately not bereft of side effects, which can make their use delicate or even dangerous.

Thus, hydroquinone, whose use is moreover limited to a concentration of 2%, is a compound that is particularly irritating and cytotoxic to the melanocyte, and whose total or partial replacement has been considered by numerous authors.

Hence the use of various natural substances including arbutoside and methylarbutoside has been considered. These arbutoside-based compositions are the subject of French Patent No. 85 04288 (2.577.805) and Japanese Patent Applications Nos. 86/152,196 and 88/011,585.

It is well established that a substance has a depigmenting effect if it acts directly on the vitality of the epidermal melanocytes where melanogenesis normally occurs and/or if it interferes with one of the stages in melanin biosynthesis, either by inhibiting one of the enzymes involved or by intercalation as a structural analog in the synthesis pathway which can accordingly be blocked, hence the depigmenting effect.

The use of topical depigmentors that have good efficacy and are harmless is particularly desirable with a view to treating regional hyperpigmentation caused by melanocytic hyperactivity such as idiopathic melasma occurring during pregnancy (mask of pregnancy or chloasma) or secondary to estrogen-progesterone contraception; local hyperpigmentation caused by benign melanocytic hyperactivity and proliferation such as lentigo senilis, known as liver spots; accidental hyperpigmentation such as postlesional photosensitization and scarring; and certain forms of leukoderma such as vitiligo where, if the injured skin cannot be repigmented, the residual zones of normal skin are depigmented to impart a homogeneous white color to the entire skin.

SUMMARY OF THE INVENTION

After a number of studies on various natural substances, it has surprisingly been found that certain arbutoside derivatives have a particularly pronounced depigmenting action that is far superior to that of arbutoside and other depigmentors such as hydroquinone and 4-hydroxycinnamic acid.

It has proved possible to demonstrate these depigmenting properties by an in vitro test showing inhibition of tyrosinase activity.

The arbutoside derivatives according to the present invention have been shown to have particularly good skin tolerance, particularly an absence of irritating effects.

Hence an object of the present invention is a cosmetic or dermatological composition with a depigmenting action containing, as an active ingredient, at least one arbutoside derivative with the following general formula:

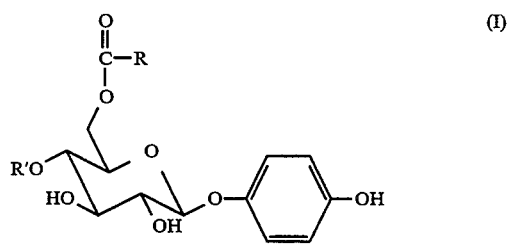

wherein:

R represents an unsaturated aliphatic or aromatic hydroxylated residue having 4 to 16 carbon atoms, and R' represents a hydrogen atom or the

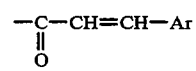

radical. Ar represents a phenyl radical that may be substituted by one or more hydroxyl groups.

DETAILED DESCRIPTION OF PREFERRED EMBODIMENTS

According to a preferred embodiment of the invention, the unsaturated aliphatic or aromatic hydroxylated residue with 4 to 16 carbon atoms is chosen from the following radicals:

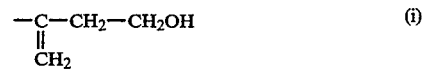

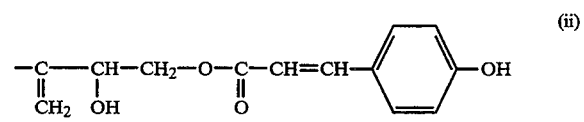

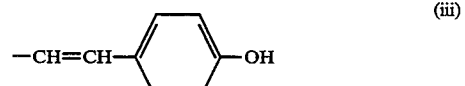

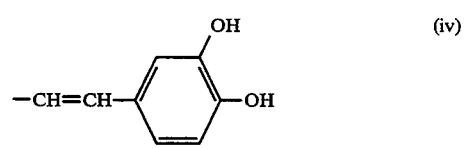

Of the arbutoside derivative in the compositions according to the invention, those particularly preferred are the following:

Compounds Nos.
(1) 6-p-coumaroylarbutoside,
(2) 6-caffeoylarbutoside,
(3) E,4-(p-hydroxycinnamoyl) -6-(4'''-hydroxy-2'''methylene butanoyl) -arbutoside,
(4) E,4''-(p-hydroxycinnamoyloxy)-6-(E,4''-(p-hydroxycinnamoyloxy)-3''hydroxy-2''methylene butanoyl)arbutoside.

Most of the compounds with general formula (I) of the compositions according to the invention have been described in the literature (Manju et al., Phytochemistry, 1977, Vol. 16, pp. 793–794). They can be obtained either by extraction from plants or by chemical synthesis by condensation on the arbutoside of the hydroxylated unsaturated acid whose hydroxy group is protected by an acetyl function.

Thus, 6-p-coumaroylarbutoside is obtained by condensation of arbutoside with p-acetoxycinnamic acid (E. Haslam, Phenolic Constituents of Vaccinium vitis-idaea, J.Chem. Soc., Suppl. I, 1964, 5649; M. Varma et al., The Synthesis of 2- and 6-O-p-coumaroyl and 6-O-p-hydroxybenzoyl arbutin derivatives, Monatsch. Chem., 1980, 111, 469; and T. Iwagawa et al., Phenolic Constituents of Viburnum carlesii, Kagoshima Daigaku Rigakubu Kiyo, Sugaku, Butsurigaku, Kagaku, 1988, 21, 89).

Likewise, 6-caffeoylarbutoside is obtained by condensation of arbutoside with 3,4-diacetoxycinnamic acid (K. Machida, et al., Phenolic Glycosides from Viburnum dilatatum, Phytochem., 1991, 30(6), 2013, and T. Iwagawa et al., Phenolic Constituents of Viburnum carlesii, Kagoshima Daigaku Rigakubu Kiyo, Sugaku, Butsurigaku, Kagaku, 1988, 21, 89).

The novel compounds (3) and (4) above were obtained from a plant rich in these compounds known as *Garnieria spathulaefolia*.

The compositions according to the invention generally contain a concentration of formula (I) active compound of between 1.5 and 38 wt. % and preferably between 1.9 and 10 wt. % relative to the total weight of the composition.

The compositions according to the invention may be in various forms, particularly aqueous or water-alcohol solutions, emulsions of the oil-in-water or water-in-oil type, or in the form of emulsified gels.

Preferably, the compositions according to the invention are in the form of a lotion, a cream, a milk, a gel, a mask, microspheres or nanospheres or vesicular dispersions, whereby the vesicles can be made of ionic lipids (liposomes) and/or nonionic lipids.

In the emulsions, the fatty phase may be comprised of a vegetable or animal oil, a mineral oil, or a synthetic oil.

Examples of suitable vegetable or animal oils, which may or may not be modified, include the following: sweet-almond oil, avocado oil, castor oil, olive oil, jojoba oil, perhydrosqualene, calophyllum oil, lanolin and its derivatives, sunflower oil, wheat germ oil, sesame oil, peanut oil, grape seed oil, soy oil, colza oil, safflower oil, coconut oil, corn oil, hazelnut oil, karite butter, fat of Shorea robusta, palm oil and apricot oil.

An example of a suitable mineral oil is vaseline oil. Examples of suitable synthetic oils include ethyl and isopropyl palmitates, alkyl myristates such as isopropyl, butyl, and cetyl myristate, hexyl stearate, the trigylcerides of octanoic and decanoic acid (for example the product sold under the name "Miglyol" by the Dynamit Nobel Company), cetyl ricinoleate, stearyl octanoate, and hydrogenated polyisobutene, as well as waxes such as ozocerite.

The fatty excipient can also contain certain compounds considered as fatty products, namely long-chain alcohols such as cetyl alcohol, stearyl alcohol, myristic alcohol, hydroxystearyl alcohol, oleic alcohol, or isostearyl alcohol.

Of the synthetic oils, silicone oils are especially suitable for use in the present invention. Of these, the silicone oil preferably used is cyclopentadimethylsiloxane, particularly the product sold under the name "Volatil Silicone 7158" by the Union Carbide Company, as well as alkyldimethicone copolyol, particularly the product sold under the name "ABIL WE 09" by the Goldschmidt Company.

The cosmetic or dermatological compositions according to the invention can optionally contain other conventional ingredients such as moisturizers, preservatives, dyes, fragrances, and penetration agents such as diethylene glycol monoether.

These compositions are applied topically in an amount corresponding to the conventional application doses for the type of composition considered (gels, creams, lotions, etc.). For example, in the case of a cream, 0.5 to 3 mg, particularly 1 to 2 mg of cream per $cm^2$ of skin are used per application, with one or two applications per day.

Preparation of compounds (3) and (4) by alcohol extraction of *Garnieria spathulaefolia*

*Garnieria spathulaefolia* is a plant belonging to the Proteaceae family growing at an altitude of 1000 m in the peridotitic uplands of northern New Caledonia.

The extract is obtained by crushing the leaves of the plant dried for 15 hours at 55° C., then soaking this coarse powder in alcohol three times at 96° C.

The alcohol phases are then combined and evaporated to dryness; from 200 g of leaf powder, 32.1 g of extract (A), namely a yield of 16% are obtained (see Table I).

Water is added to extract (A) and it is agitated for 2 hours, after which the suspension is filtered. The water-soluble fraction is extracted seven times with ethyl acetate. The ethyl acetate-soluble fraction is removed, rinsed with water, then evaporated to dryness to yield 4 g of product (B). This fraction (B) is partially (3 g) subjected to chromatography on a silica column using an AcOEt-$CH_2Cl_2$-MeOH mixture in a ratio of 8:3:1, then 0:12:1, then 0:4:1 as the eluant. This chromatography produces several fractions including fraction 77E, which is in turn subjected to reversed-phase chromatography on silica. Thus, compound (3) (66 mg) and compound (4) (48 mg) are obtained.

The two compounds have the following physical chemistry characteristics:

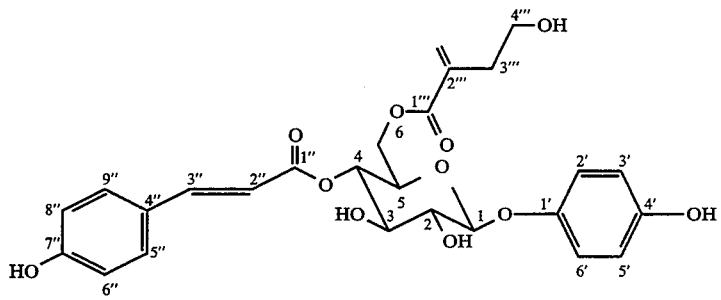

Compound (3)

E,4-(p-hydrycinnamoyl)-6-(4'''-hydroxy-2'''-methylene butanoyl)-arbutoside
Molecular formula $C_{26}H_{28}O_{11}$
$[\alpha]_D^{25°\ C.} = -14.6°$ (C=0.5 in MeOH)
Mol. wt. 516
UV spectrum
λ (EtOH) nm 211, 250, 313
Infrared spectrum (KBr, $cm^{-1}$):1061, 1159, 1215, 1441, 1518, 1602, 1714, 2950.
Mass spectrum
(FAB):539 $(M+Na)^+$
NMR spectrum of $^1H$ (400 MHz, $CD_3OD$)

| δ (ppm) | | J(Hz) | proton |
|---|---|---|---|
| 7.70 | 1H | d | 16 | H-3'' |
| 7.50 | 2H | d | 9.0 | H-5'',9'' |
| 6.95 | 2H | d | 9.0 | H-2',6' |
| 6.80 | 2H | d | 9.0 | H-6'',8'' |
| 6.70 | 2H | d | 9.0 | H-3',5' |
| 6.40 | 1H | d | 16 | H-2'' |
| 6.25 | 1H | d | 1.5 | =CHaHb |
| 5.75 | 1H | d | 1.5 | =CHaHb |
| 5.00 | 1H | t | 9.0 | H-4 |
| 4.85 | 1H | d | 8.0 | H-1(β) |
| 4.35 | 1H | dd | 13.3 | H-6a |
| 4.25 | 1H | dd | 13.6 | H-6b |
| 3.90 | 1H | m | | H-5 |
| 3.75 | 1H | t | 9.0 | H-3 |
| 3.65 | 2H | t | 6.5 | CH2—CH2OH |
| 3.55 | 1H | m | | H-2 |
| 2.55 | 2H | t | 6.5 | CH2—CH2OH |

NMR spectrum of $^{13}C$ (50 MHz, $CD_3OD$ δ ppm)
168.33(C-1'''); 167.98(C-1''); 161.37(C-7''); 154.00(C-1'); 152.12(C-4'); 147.42(C-3''); 138.42(C-2'''); 131.31(C-5'',9''); 128.17(=CH2); 127.10(C-4''); 119.6-1(C-2'',6''); 116.86(C-3',5'); 116.68(C-6'',8''); 112.30(C-2); 103.52(C-1); 75.58(C-4); 75.038(C-3); 73.30(C-2); 72.33(C-5); 64.40(C-6); 61.57(C-4'''); 36.21(C-3''').

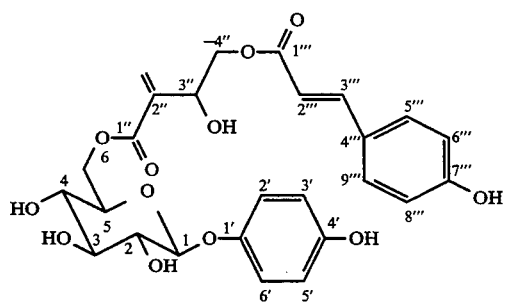

Compound (4)

6-(E,4''-(p-hydroxycinnamoyloxy)-3''hydroxy-2''methylene butanoyl)arbutoside
Molecular formula $C_{26}H_{28}O_{12}$
$[\alpha]_D^{25°\ C.} = -38.2°$ (C=0.5 in MeOH)
UV spectrum
λ max (EtOH) nm 209, 250, 313
Infrared spectrum (KBr, $cm^{-1}$):1082, 1180, 1216, 1271, 1518, 1595, 1715, 2950.
Mass spectrum
(FAB) :555 $(M+Na)^+$
NMR spectrum of $^1H$ (400 MHz, $CD_3OD$)

| δ (ppm) | | J(Hz) | proton |
|---|---|---|---|
| 7.55 | 1H | d | 16 | H-3'' |
| 7.37 | 2H | d | 9.0 | H-5''',9''' |
| 6.90 | 2H | d | 9.0 | H-2',6' |
| 6.75 | 2H | d | 9.0 | H-6''',8''' |
| 6.62 | 2H | d | 9.0 | H-3',5' |
| 6.37 | 1H | s | | =CHaHb |
| 6.28 | 1H | d | 16 | =H-2''' |
| 6.05 | 1H | s | | =CHaHb |
| 4.77 | 1H | m | | H-3'' |
| 4.72 | 1H | d | 8.0 | H-1 |
| 4.55 | 1H | dd | 12.3 | H-6a |
| 4.20 | 3H | m | | H-6b,CH2-4'' |
| 3.65 | 1H | m | | H-5 |
| 3.42 | 2H | m | | H-2,3 |
| 3.35 | 1H | m | | H-4 |

NMR spectrum of $^{13}C$ (50 MHz, $CD_3OD$ δ ppm)
168.90(C-1'''); 167.10(C-1'''); 161.53(C-7'''); 154.01(C-1'); 151.49(C-4'); 146.72(C--3'''); 141.62(C-2'''); 131.69(C-5''',9'''); 127.27(=CH2); 127.27(C-4'''); 119.62(C-2'',6''); 116.70(C-6''',8'''); 116.67(C-3',5'); 103.42(C-1); 77.86(C-3); 75.22(C-5); 74.8-2(C-2); 71.82(C-4); 69.29(C-3''); 68.12(C-4''); 65.20(C-6).

TABLE I

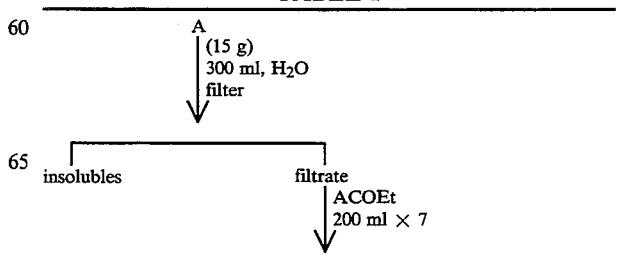

TABLE I-continued

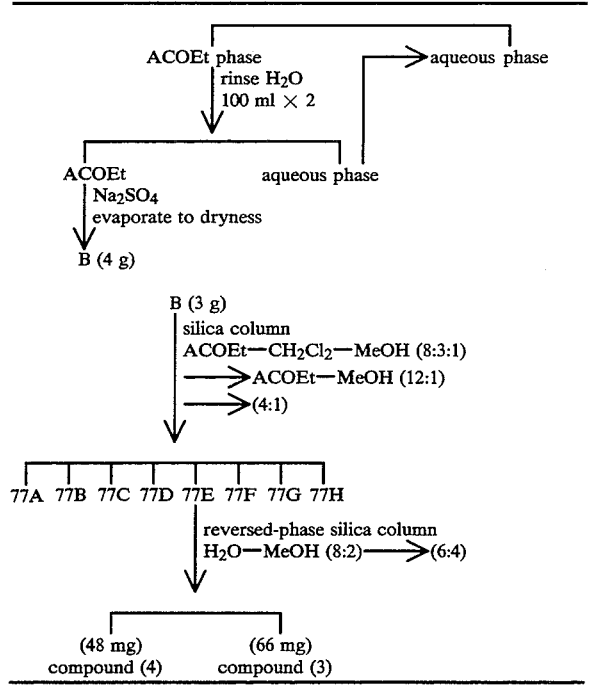

Cosmetic or Dermatological Compositions

EXAMPLE 1

Lotion

| | |
|---|---|
| Alcohol | 50 g |
| Polyoxyethylene glycol (PEG-8) | 30 g |
| Ethoxydiglycol | 5 g |
| Glycerin | 5 g |
| Water | 3 g |
| 6-p-coumaroylarbutoside | 7 g |

EXAMPLE 2

Water-in-oil emulsion

| | |
|---|---|
| Glycerin | 10 g |
| Propylene glycol | 5 g |
| 6-p-coumaroylarbutoside | 3 g |
| Cyclopentadimethylsiloxane | 20 g |
| Polydimethylsiloxane polyoxyethylene | 3 g |
| Fragrance | 0.1 g |
| Preservatives | qs. |
| Water | qs. 100 g |

EXAMPLE 3

Oil-in-water emulsion

| | |
|---|---|
| Polyethylene glycol ether from cetearyl alcohol | 1 g |
| Glyceryl stearate | 3 g |
| Cocoa caprylate/caprate (esters of acids with $C_8$–$C_{10}$ and fatty alcohols with $C_{12}$–$C_{18}$) | 5 g |
| Acrylic polymer (Carbomer 934 sold by the Goodrich Company) | 0.3 g |
| Triethanolamine (50%) | 0.9 g |
| Alcohol | 20 g |
| 6-p-coumaroylarbutoside | 2 g |
| Glycerin | 3 g |
| Preservative | qs. |
| Fragrance | qs. |
| Water | qs. 100 g |

EXAMPLE 4

Preparation of liposomes in solution formulation

The following products are weighed out into a 1-liter round-bottomed flask:

| | |
|---|---|
| Soy lecithin: lipoid S75 (sold by the Lipoid Company) | 3.0 g |
| 6-p-coumaroylarbutoside | 0.3 g | and dissolved in 100 ml of a mixture of chloroform and methanol solvents in a 2:1 ratio.

The solvent is then evaporated with a rotary evaporator and the last traces of solvent are removed by exposure to a vane pump for one hour. The combination of lipids obtained is contacted with 60 g of demineralized water containing 1 g of glycerin, and the mixture is homogenized at 40° C. ion a Virtis homogenizer.

The formula is completed by adding the following substances:

| | |
|---|---|
| Methyl parahydroxybenzoate | 0.2 g |
| Mixture of carboxyvinyl acids "Carbopol 940" | 0.1 g |
| Triethanolamine | qs. pH = 6 |
| Water | qs. 100 g |

This yields an opalescent solution which is fluid but does not flow.

EXAMPLE 5

Preparation of nonionic vesicles in a cream formulation

The following products are weighed out into a 100-ml round-bottom flask:

| | |
|---|---|
| Nonionic lipid with formula: $C_{12}H_{25}\text{--}[OC_2H_3(R)]\text{--}O\text{--}[C_3H_5(OH)\text{--}O]_{\bar{n}}\text{--}H$ where $\text{--}OC_2H_3(R)\text{--}$ comprises a mixture of radicals: 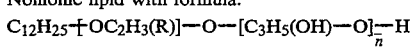 where $\text{--}C_3H_5(OH)\text{--}O\text{--}$ comprises a mixture of radicals: 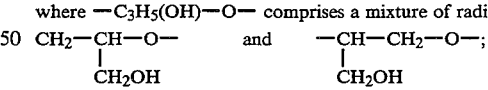 where $\bar{n} = 6$; and where R is a mixture of $C_{14}H_{29}$ radicals and $C_{16}H_{33}$ | 0.9 g |
| Sodium acylglutamate HS21 (sold by the Ajinomoto Company) | 0.1 g |
| 6-p-coumaroylarbutoside | 0.1 g | and dissolved in 30 ml of a mixture of chloroform-methanol solvents in a ratio of 2:1.

The solvent is evaporated with the aid of a rotary evaporator and the last traces of solvent are removed by contact with a vane pump for one hour.

The combination of lipids obtained is contacted with 40 g of demineralized water containing 3 g of glycerin, and the mixture is homogenized at 40° C. with a Virtis homogenizer.

Ten grams of perhydrosqualene is then added and the mixture is homogenized at room temperature with the Virtis.

The formula is completed by adding the following substances:

| | |
|---|---|
| methylparahydroxybenzoate | 0.2 g |
| Mixture of carboxyvinyl acids "Carbopol 940" | 0.4 g |
| Triethanolamine | qs. pH = 6 |
| Water | qs. 100 g |

This produces a thick, white cream.

While the present invention has been disclosed in connection with preferred embodiments thereof, it should be appreciated that there are other embodiments of the present invention which fall within the spirit and scope of the present invention as defined by the appended claims.

What is claimed is:

1. A cosmetic or dermatological composition with a depigmenting action, comprising a cosmetically or dermatologically acceptable excipient and, as an active ingredient, an arbutoside derivative with the following formula:

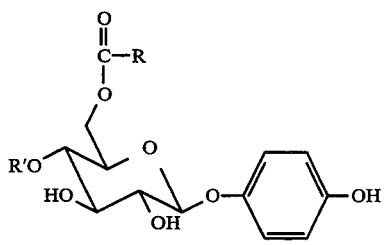
(I)

wherein:

R' represents a hydrogen atom or the

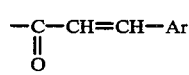

radical, where Ar represents a phenyl radical substituted by at least one hydroxyl group, and R is an unsaturated aliphatic or aromatic hydroxylated residue selected from the group consisting of:

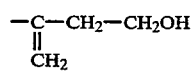
(i)

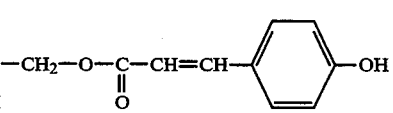
(ii)

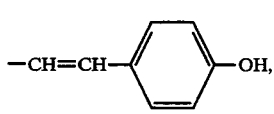
(iii)

and

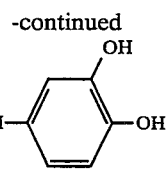
(iv)

2. A composition according to claim 1, wherein the arbutoside derivative is selected from the group consisting of:
   6-p-coumaroylarbutoside,
   6-caffeoylarbutoside,
   E,4-(p-hydroxycinnamoyl) -6-(4'''-hydroxy-2'''methylene butanoyl) -arbutoside, and
   6-(E,4''-(p-hydroxycinnamoyloxy)-3''hydroxy-2''methylene butanoyl)arbutoside.

3. A composition according to claim 1, wherein the arbutoside derivative is present in a concentration of between 1.5 and 38 wt. % relative to the total weight of the composition.

4. A composition according to claim 1, wherein the arbutoside derivative is present in a concentration of between 1.9 and 10 wt. % relative to the total weight of the composition.

5. A composition according to claim 1, further comprising a cosmetic or dermatological ingredient selected from the group consisting of moisteners, perservatives, dyes, fragrances, and penetration agents.

6. A method of cosmetic or dermatological treatment of skin comprising applying to skin to be depigmented a composition comprising a cosmetically or dermatologically acceptable excipient and, as an active ingredient, an arbutoside derivative with the following formula:

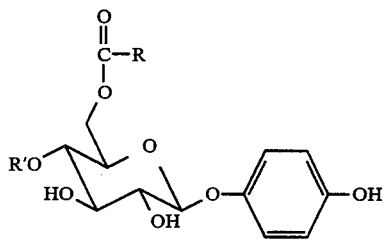
(I)

wherein:

R' represents a hydrogen atom or the

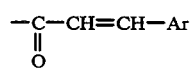

radical, where Ar represents a phenyl radical substituted by at least one hydroxyl group, and R is an unsaturated aliphatic or aromatic hydroxylated residue selected from the group consisting of:

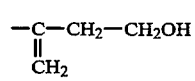
(i)

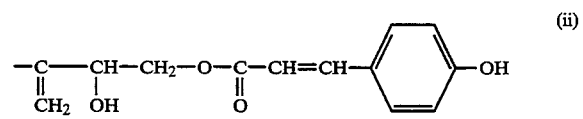
(ii)

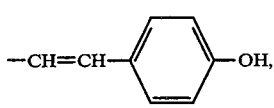

and

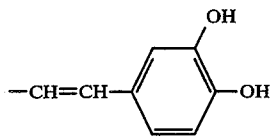

7. A method according to claim 6, wherein the arbutoside derivative is selected from the group consisting of:

6-p-coumaroylarbutoside, 6-caffeoylarbutoside,

E,4-(p-hydroxycinnamoyl) -6-(4'''-hydroxy-2'''methylene butanoyl) -arbutoside, and 6-(E,4''-(p-hydroxycinnamoyloxy)-3''hydroxy-2''methylene butanoyl)arbutoside.

8. A method according to claim 6, wherein the arbutoside derivative is present in a concentration of between 1.5 and 38 wt. % relative to the total weight of the composition.

9. A method according to claim 6, wherein the arbutoside derivative is present in a concentration of between 1.9 and 10 wt. % relative to the total weight of the composition.

10. A method according to claim 6, wherein said composition further comprises a cosmetic or dermatological ingredient selected from the group consisting of moisteners, perservatives, dyes, fragrances, and penetration agents.

* * * * *